United States Patent [19]

Merz

[11] Patent Number: 4,861,772
[45] Date of Patent: Aug. 29, 1989

[54] METHOD AND COMPOSITION TO TREAT PANIC SYNDROME

[75] Inventor: Walter Merz, Basel, Switzerland

[73] Assignee: Hoffmann-La Roche Inc., Nutley, N.J.

[21] Appl. No.: 178,671

[22] Filed: Apr. 7, 1988

[30] Foreign Application Priority Data

Jan. 27, 1988 [CH] Switzerland ............................ 272/88

[51] Int. Cl.$^4$ .............................................. A61K 31/55
[52] U.S. Cl. ...................................... 514/219; 514/218
[58] Field of Search ........................ 514/218, 220, 219

[56] References Cited

U.S. PATENT DOCUMENTS 4,352,815 10/1982 Hunkeler et al. .................... 514/219

Primary Examiner—Stanley J. Friedman
Attorney, Agent, or Firm—Jon S. Saxe; Bernard S. Leon; William G. Isgro

[57] ABSTRACT

The known compound, t-butyl (S)-8-bromo-11,12,13,13a-tetrahydro-9-oxo-9H-imidazo[1,5-a]pyrrolo[2,1-c][1,4]benzodiazepine-1-carboxylate of the formula

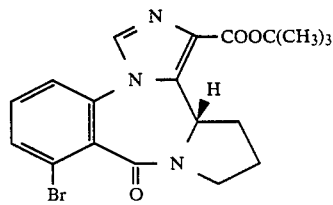

is effective in the prevention or interruption in a human being of panic states, accompanying phobias and the associated social consequences such as anticipatory anxiety and avoidance behavior. In particular, it is effective in the discontinuous, purely attack-based prevention or interruption of panic states.

4 Claims, No Drawings

METHOD AND COMPOSITION TO TREAT PANIC SYNDROME

BRIEF DESCRIPTION OF THE INVENTION

The invention relates to the use of t-butyl (S)-8-bromo-11,12,13,13a-tetrahydro-9-oxo-9H-imidazo[1,5-a]pyrrolo[2,1-c][1,4]benzodiazepine-1-carboxylate of the formula

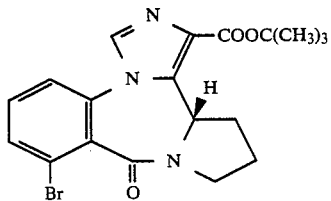

which is referred to hereinafter as compound A, in the prevention or interruption of panic states in human beings, accompanying phobias and the associated social consequences, such as, anticipatory anxiety and avoidance behavior. In particular, it relates to the use of compound A in the discontinuous, purely attack-based prevention or interruption of panic states.

DETAILED DESCRIPTION OF THE INVENTION

The present invention is concerned with the use of t-butyl (S)-8-bromo-11,12,13,13a-tetrahydro-9-oxo-9H-imidazo[1,5-a]pyrrolo[2,1-c][1,4]benzodiazepine-1-carboxylate of the formula

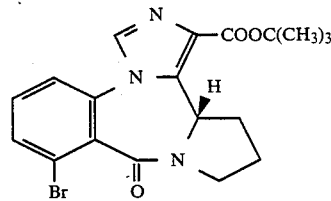

which is referred to hereinafter as compound A, in the prevention of interruption of panic states in a human being or host, accompanying phobias and the associated social consequences, such as, anticipatory anxiety and avoidance behavior. In particular, it is concerned with the use of compound A in the discontinuous, purely attack-based prevention or interruption of panic states.

Objects of the invention comprise the use of compound A in the prevention ot interruption of panic states, accompanying phobias and the associated social consequences, such as anticipatory anxiety and avoidance behavior, and for the preparation of medicaments for the prevention or interruption of panic states, accompanying phobias and the associated social consequences, such as anticipatory anxiety and avoidance behavior, as well as a method and medicaments for the treatment of panic states, accompanying phobias and the associated social consequences, such as anticipatory anxiety and avoidance behavior.

Compound A is a known substance, its preparation and its known anticonvulsive and anxiolytic properties are described, for example, in European Patent Publication No. 59 391.

Panic states or attacks are onsets of acute anxiety, accompanied or even dominated by somatic anxiety equivalents such as a sensation of suffocation, palpitations or racing of the heart, fainting attacks, sensation of dizziness, sensoric loss of sensations (paresthesias), stomach pains and the like. They are characterized by a rapid increase of the symptomatics, within a few minutes and of relatively short duration, generally up to one hour. Panic states can occur spontaneously because of biochemical disorders in the brain or, when phobias are present, can be caused by anticipation or the presence of phobic stimuli. Typical phobic stimuli are crowds, public or private transport, open or empty spaces or rooms, closed rooms, the sensation of being alone, public appearances, and the like. The psychological combination of panic states with certain situations of the kind described can lead to an avoidance behavior vis-a-vis these situations. In very severe cases the patient is unable to leave his/her home. These conditions are accompanied by depression and anticipatory anxiety in the interval between the panic states.

Various therapies have already been tried. In particular, various kinds of psychotherapy, such as, behavior therapy and cognitive therapy, and medicinal therapy are in use. Panic states are treated medicinally with tricyclic antidepressants, monoamine oxidase inhibitors, such as, MAO inhibitors or triazolobenzodiazepines. Conventional benzodiazepines have also been used, but have proved to be ineffective.

The aforementioned medicaments are administered in high dosages in continuous long-term therapy. Disadvantages of the tricyclic antidepressants and the MAO inhibitors are the frequent side effects, the slow onset of activity and the poor compliance by the treated patients. Disadvantages of the use of triazolobenzodiazepines in the aforementioned type of approach are frequent and lasting sedating side effects as well as the frequently occurring drug dependence with the consequence of obstinate withdrawal syndromes.

A major disadvantage of the described conventional pharmacotherapies lies in that an apparent disparity exists between the duration of the panic state, on average a few minutes to several hours per week, and the duration of high drug concentrations, 7 day per week. This leads in turn to side effects in the interval between successive panic attacks and, in the case of the triazolobenzodiazepines, additionally to physical dependence with the corresponding withdrawal problems.

Against the panic state, in the ideal situation effective plasma levels of a medicament should be used during the first prodromi of the commencing panic attack and should not last longer than that. The activity of this plasma level should be sufficiently large to suppress or to markedly reduce the commencing attack from the outset. Prerequisite for this are a specific antipanic activity, a very rapid adsorption even in the case of non-invasive application, and a short elimination half-life of the required medicament.

It has surprisingly been found that compound A possesses these characteristics and can therefore be used for the discontinuous, purely attack-based therapy of the panic syndrome. After 1 mg of compound A has been taken perorally in tablet form a maximal active substance level is already reached after 45 minutes. Clinically relevant effects, that is, effects noticed by patients, generally occur already after 10 minutes. The β-half life of compound A is only 2 hours and 15 minutes.

Compound A displays a specific antipanic activity even in low dosages and need not be taken continuously over a long period, as is the case with the aforementioned medicaments.

In a preferred embodiment, the therapy, that is, the taking of the medicament by the patient, is controlled by the occurrence of a panic attack or the anticipation that a panic attack will occur, in contrast to the conventional continuous therapy which is controlled by daily routine, for instance, the medicament is taken in the morning and/or evening. The chosen administration form and dosage of compound A is taken at the first signs of the commencing of an attack or in the anticipation of a phobic situation which is usually connected with panic states. A clear interval of from one hour to several months can exist between two successive intakes of the medicament. This mode of administration is characterized by a discontinuous plasma level of the medicament and/or its metabolites, that is, by regular and/or irregular periods in the course of the treatment during which the patient is not under the direct influence of the medicament. An indirect psychological influence of the medicament that is, the awareness that panic attacks can be prevented or suppressed results in the consequences of the panic attacks, such as anticipatory anxiety, depression, phobias and phobic avoidance behavior, decreasing or disappearing also in the medicament-free interval between the panic states.

The advantage of this therapy therefore exits in the economical use of the medicament which is as infrequent as possible with the result that undesired side effects seldom occur, but primarily to prevent the occurrence of a physical dependence tied to the level of duration of the medicament and the facilitated interruption of the drug therapy which is therapy provided.

The dosage of compound A required for the prevention or interruption of a panic state depends on the route of administration, the dosage form and the age, the weight and the general condition of the patient and will, of course, be fitted to the individual requirements in each particular case. In the case of oral administration, the dosage is in the range of from about 0.1 to about 2.0 mg, pre panic attack.

The results of a clinical study will be referred to as an example of the use and the effect of discontinuous therapy of panic attacks by means of compound A.

The clinical study is a double-blind, parallel group study in which in each case 12 patients with panic syndrome were treated either with compound A, that is, tablets containing 0.5 mg of active substance or with a corresponding placebo. The course of the trial was the following. After examining the inclusion and exclusion criteria and recording the basic data, the patients each received 20 tablets with instructions to take one tablet at the approach or beginning of the next panic attack. The medicaments previously used had been withdrawn before the commencement of the study. In the case of a satisfactory outcome of treatment the initial dosage was to be used a once more. Then, for the second investigation, the investigator was to be consulted. In the case of an unsatisfactory outcome of therapy, the dosage in the case of the second panic attack was to be increased to two tablets, which dosage was to be repeated in the case of success and, in the case of failure, was to be increased to three tablets. As soon as the most suitable dosage had been found or three tablets had been found to be ineffective, the investigator was to be consulted for the third investigation. Patients with ineffective medication were to be discharged from the trial. Patients in whom an effective dosage had been found would use that dose in the next twelve panic states. In cases in which withdrawal phenomena of the preceding treatment played a role, the twelve treatments of the main treatment phase can be extended with an additional twelve dosages in a further phase, additional phase.

During the treatment, the patients were required to carry a treatment day book. On the basis of the remarks contained therein, the statements of the patients as well as specific observations, the results of the trial at the end of the titration phase (investigation 2), at the end of the main treatment phase (investigation 3) and, if desired, at the end of the additional phase (investigation 4) were introduced into the trial data by the investigator. The following psychiatric scales were filled out as standardized comparative investigations at all points in time of the trial: anxiety scale according to Covi, depression scale according to Raskin, self-evaluated anxiety scale (SAS) and self-evaluated depression scale (SDS) according to Zung, as well as the withdrawal symptom scale (WSS) according to Merz & Ballmer.

The following data were obtained. In each case, 12 patients were treated with compound A or placebo. In the group treated with compound A, 7 were male and 5 female with an average age of $33\pm5.4$ years, of which—according to the DSM-III classification—2 suffered from panic syndrome without agoraphobia and 10 suffered from panic syndrome with agoraphobia. The diagnosis of a major depression was also established in 6 cases. The placebo group contained 6 males and 6 females with an average age of $40\pm10.5$ years, of which all 12 had the diagnosis panic syndrome with agoraphobia, but only three showed the additional diagnosis of major depression.

The average duration of the disorder amounted to $98\pm83$ months in the group treated with compound A and to $143\pm164$ months in the placebo group. The weekly frequency of panic states was $5.6\pm3.2$ in the group treated with compound A and $7.6\pm5.6$ in the placebo group. In this calculation, a runaway in the placebo group which fell outside the average value and the five-fold standard deviation was not taken into consideration. The average duration of the panic attacks was $27\pm17$ minutes in the group treated with compound A and $25\pm16$ minutes in the placebo group. Nine (9) patients treated with compound A and 10 placebo patients were able to predict attacks with an average prediction time of $11\pm12$ minutes in the group treated with compound A and $10\pm7$ minutes in the placebo group. The additional parameters also showed comparable initial values.

Because of the different lengths of the total treatment, average duration $43\pm27$ days in the group treated with compound A and $28\pm32$ days in the placebo group and because of the unequal distribution of the exclusions and drop-outs, the following results are presented in the form of an end point analysis:

| Variable | Compound A | Placebo | Significance |
|---|---|---|---|
| Average number of tablets at the end of treatment | $1.4 \pm 0.9$ | $2.7 \pm 0.7$ | $p < 0.001$ |
| Average treatment period (days) | $43 \pm 27$ | $28 \pm 34$ | $p < 0.05$[1] |
| Drop-outs caused by ineffectiveness (n) | 1 | 8 | $p = 0.0094$[2] |
| $\Delta$ frequency of attack per week (n) Reduction in the | $-2.6 \pm 3.3$ | $+1.1 \pm 9.8$ | $p < 0.05$ |

-continued

| Variable | Compound A | Placebo | Significance |
|---|---|---|---|
| intensity of attack (4 = complete, 3 = strong 2 = weak, 1 = no effect) | 3.5 ± 0.9 | 1.7 ± 1.2 | $p < 0.01$ |
| Δ Covi anxiety scale (outside evaluation) | 3.3 ± 3.2 | 1.8 ± 3.0 | $p < 0.001$ |
| Δ Zung anxiety scale (self evaluation) | 6.4 ± 8.5 | 5.6 ± 9.6 | $p < 0.001$ |
| Δ Raskin depression scale (outside evaluation) | 1.9 ± 3.2 | 1.1 ± 2.1 | $p < 0.001$ |
| Δ Zung depression scale (self evaluation) | 4.5 ± 9.0 | 2.9 ± 9.1 | $p < 0.001$ |
| Δ withdrawal symtom scale (WSS) | −3.9 ± 6.8 | −3.1 ± 8.0 | n.s. |
| Average improvement in phobias scale as initial intensity) | 2.2 ± 1.0 | 1.8 ± 1.2 | $p < 0.001$ |

[1]Mann-Whitney U test
[2]Exact test according to Fisher. Remaining analyses:
T-test for independent random checks.

The comparative value list presented above shows that compound A has not only a specific antipanic activity, but also that secondary panic symptoms in untreated intervals between successive panic attacks are reduced significantly better than by placebo.

The following side effects were found:

| | Compound A | | | Placebo | | |
|---|---|---|---|---|---|---|
| | MRA[3] | No Reg. | No Pat. | MRA No. | No Reg. | No Pat. |
| Dopiness | 21.8% | 60 | 5 | 7.1% | 6 | 2 |
| Drowsiness | 16.4% | 45 | 9 | 3.6% | 3 | 2 |
| Irresistible sleep | — | — | — | 2.4% | 2 | 1 |
| Impaired concentration | — | — | — | 1.1% | 1 | 1 |
| Unsteadiness when walking or standing | 4.7% | 13 | 4 | — | — | — |
| Coarse muscular relaxation | 0.7% | 2 | 1 | 2.4% | 2 | 1 |
| Slurred speech/ "heavy tongue" | 1.8% | 5 | 2 | — | — | — |
| Nausea | 3.3% | 9 | 1 | — | — | — |
| Headache | 0.7% | 2 | 1 | — | — | — |
| Dry mouth | 0.7% | 2 | 1 | — | — | — |
| Burning tongue | — | — | — | 2.4% | 2 | 1 |

[3]MRA = "Mean Risk per Administration", i.e. the risk at which the particular side effect is incurred by a single intake of the medicament.

Towards the end of the study most of the side effects were weaker or had disappeared completely.

From the list of side effects, it is evident that the placebo has less benzodiazepine-typical side effects of the sedative and motor type. All together, compound A has, however, a satisfactory tolerance, since the observed side effects were in total only of minimal quality, CGI evaluation, and of short duration, on average a total of 7.8±7.6 hours or 0.96±1.01% of the total treatment period.

In the scope of the invention, compound A is preferably used in the form of perorally administerable pharmaceutical compositions, for example, in the form of tablets, coated tablets, dragees, hard and soft gelatin capsules, solutions, emulsions or suspensions. Tablets are the preferred dosage form.

For the preparation of pharmaceutical compositions, compound A is processed with pharmaceutically inert, inorganic or organic carriers. As such carriers there can be used for tablets, coated tablets, dragees and hard gelatine capsules, for example, lactose, maize starch or derivatives thereof, talc, stearic acid or its salts and the like. Suitable carriers for soft gelatin capsules are, for example, vegetable oils, waxes, fats, semi-solid and liquid polyols and the like. Suitable carriers for the preparation of solutions and syrups are, for example, water, polyols, saccharose, invert sugar, glucose and the like.

The pharmaceutical compositions can also contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances.

The following Example describes a suitable dosage form for the practical application of the present invention. However, it is not intended to limit the scope of suitable dosage forms in any manner.

| Example | |
|---|---|
| Compound A | 0.5 mg |
| Lactose | 126.5 mg |
| Maize starch | 54.0 mg |
| Povidone K30 | 8.0 mg |
| Na carboxymethylstarch | 10.0 mg |
| Magnesium stearate | 1.0 mg |
| | 200.0 mg |

Compound A, lactose and maize starch are mixed and granulated with an aqueous and/or alcoholic solution of Povidone$^{K30}$. The dried and crushed granulate is mixed with Na carboxymethylstarch and magnesium stearate and subsequently pressed into tables weighing 200 mg.

I claim

1. A method for the prevention or interruption of panic states, accompanying phobias and the associated social consequences, including anticipatory anxiety and avoidance behavior, in a host with panic syndrome, which method comprises administering perorally to such a host an effective amount of t-butyl (S)-8-bromo-11,12,13,13a-tetrahydro-9-oxo-9H-imidazo [1,5-a]pyrrolo[2,1-c][1,4]benzodiazepine-1-carboxylate.

2. A method for the discontinuous, purely attack-based prevention or interruption of panic states, in a host with panic syndrome, which comprises administering perorally to such a host, in the anticipation of a phobic situation usually associated with panic states or at the first indication of commencing panic state, an effective amount of t-butyl (S)-8-bromo-11,12,13,13a-tetrahydro-9-oxo-9H-imidazo [1,5-a]pyrrolo-[2,1-c][1,4]benzodiazepine-1-carboxylate.

3. A method in accordance with claim 1, wherein the effective amount is in the range of from about 0.1 mg to about 2.0 mg, per panic attack.

4. A method in accordance with claim 2, wherein the effective amount is in the range of from about 0.1 mg to about 2.0 mg, per panic attack.

* * * * *